United States Patent [19]

Cané et al.

[11] Patent Number: 5,015,185
[45] Date of Patent: May 14, 1991

[54] DEVICE FOR EXTRACTING DENTAL PROSTHESES, CROWNS AND THE LIKE

[76] Inventors: Davide Cané, Via XXV Aprile 10², 40055 Castenaso; Giancarlo Venturi, Via Nazionale, 60, 40067 Rastignano, both of Italy

[21] Appl. No.: 410,213
[22] Filed: Sep. 21, 1989
[51] Int. Cl.⁵ .............................................. A61C 3/14
[52] U.S. Cl. ................................... 433/159; 433/153
[58] Field of Search ............... 433/159, 160, 161, 157, 433/158, 153

[56] References Cited

U.S. PATENT DOCUMENTS 1,094,269 4/1914 Taylor ................................. 433/157

FOREIGN PATENT DOCUMENTS

| 7738 | 2/1894 | Fed. Rep. of Germany | 433/159 |
| 581005 | 7/1933 | Fed. Rep. of Germany | 433/160 |
| 323504 | 12/1934 | Italy | 433/159 |
| 965428 | 10/1982 | U.S.S.R. | 433/157 |

Primary Examiner—Cary E. Stone
Assistant Examiner—Michael Lynch
Attorney, Agent, or Firm—Guido Modiano; Albert Josif

[57] ABSTRACT

The device for extracting dental crowns has two levers, each having a handgrip and a jaw. The levers are pivotally connected so that the jaws are moved apart by moving the handgrips closer together. A body is articulated to one of the jaws and guided in a seat of the other jaw, and supports two opposite hook-like elements which oscillate in a plane perpendicular to the plane of the levers. The other jaw has abutments adapted to rest on teeth adjacent the crown to be extracted. In the position of mutual approach of the jaws, the hook-like elements engage the edges of the crown so that by acting on the levers a force is exerted for the extraction of the crown against the resting reaction of the abutments on the adjacent teeth.

3 Claims, 1 Drawing Sheet

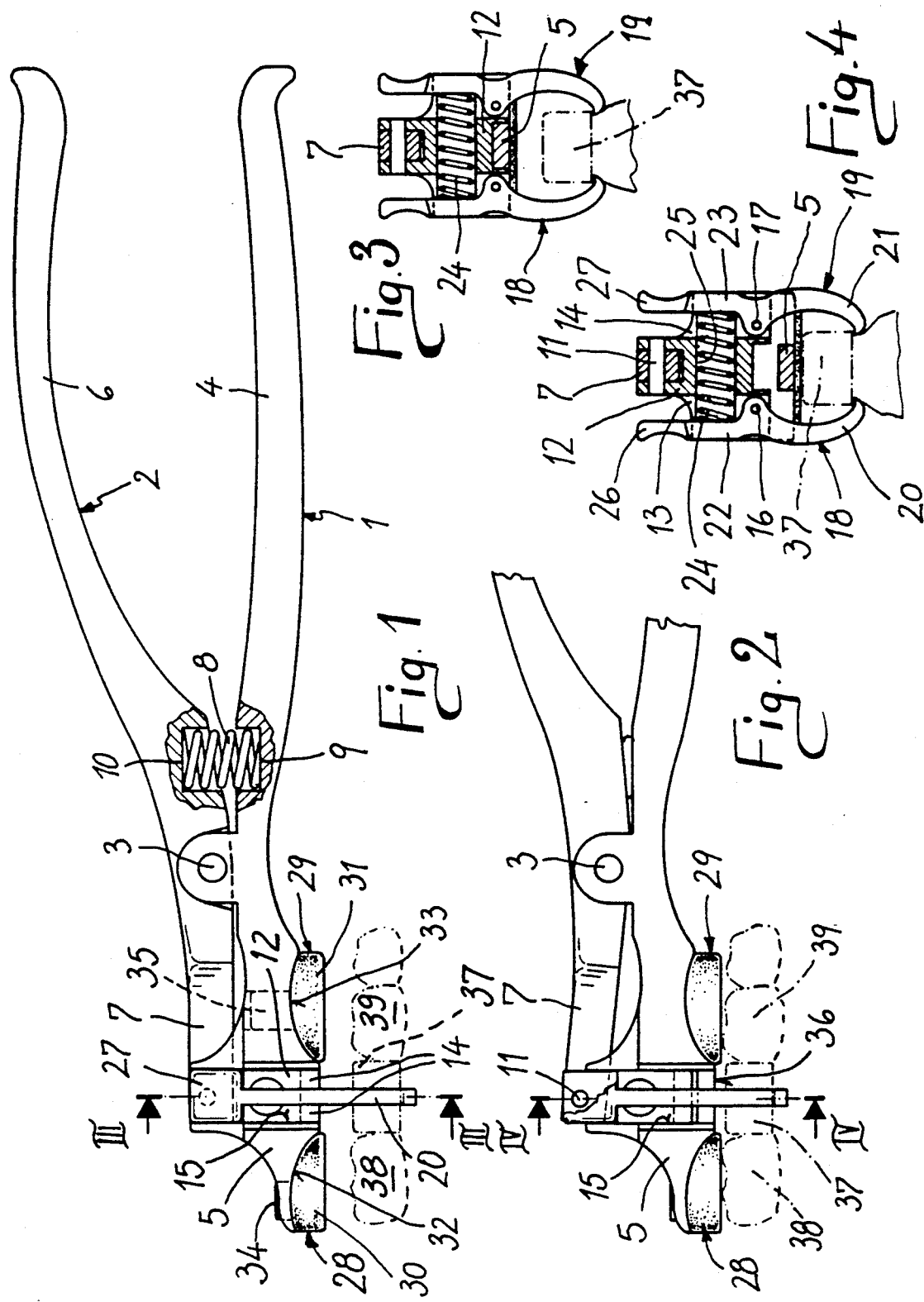

DEVICE FOR EXTRACTING DENTAL PROSTHESES, CROWNS AND THE LIKE

BACKGROUND OF THE INVENTION

The present invention relates to a device for extracting dental prostheses, crowns and the like.

As known, in the field of dentistry it is often necessary to remove an artificial crown which has been applied to protect and cover a damaged tooth or to support a prosthesis of a lost or extracted tooth.

Crowns are currently removed by resorting to rather empirical extractors which, in use, are not always tolerated by the patient due to the force which has to be applied in order to overcome the strength of the bond between such artificial crowns or prostheses and the tooth's natural crown by virtue of the interposition of adhesives which impart a strong anchorage.

SUMMARY OF THE INVENTION

The aim of the present invention is therefore to provide a device which permits the extraction of dental crowns or prostheses in a simpler and less traumatic manner than the devices currently in use.

Within the scope of this aim, an object of the present invention is to provide a device for extracting dental prostheses, crowns and the like which is easy to use and which facilitates operation within the oral cavity, in which access and freedom to maneuver an instrument are limited.

This aim and object and other objects and advantages of the invention which will become apparent hereinafter, are achieved by a device which is characterized in that it comprises two levers each having a handgrip and a jaw, said levers being pivotally connected so that said jaws are moved apart when the handgrips are moved towards each other, a body being articulated to one of said jaws, said body being guided within a seat provided on the other jaw and supporting two opposite hook-like elements pivoted in a plane perpendicular to the plane of said levers, said other jaw having abutments adapted to rest on a mouth zone adjacent to a prosthesis to be extracted, said hook-like elements being adapted to engage an edge of said prosthesis when said jaws are moved towards each other and to exert an extraction force against the resting reaction of the abutments on the teeth when the jaws are moved apart.

BRIEF DESCRIPTION OF THE DRAWINGS

Further features and advantages of the present invention will become apparent from the following detailed description on the basis of the accompanying drawings, wherein:

FIG. 1 is a side view of the device in the position in which it engages a crown;

FIG. 2 is a partial side view of the device in the position in which it extracts the crown;

FIG. 3 is a sectional view taken along the plane III—III of FIG. 1; and finally

FIG. 4 is a sectional view taken along the plane IV—IV of FIG. 2.

DESCRIPTION OF THE PREFERRED EMBODIMENT

With reference to the above described figures, the device comprises a pair of levers 1, 2 mutually pivoted at a pin 3.

The lever 1 comprises a shaped handgrip 4 which extends beyond the fulcrum 3 and defines a jaw 5.

The lever 2 similarly comprises a shaped handgrip 6 and a jaw 7.

Said levers 1, 2 are pivotally connected so that when the handgrips 4, 6 are moved mutually closer the jaws 5, 7 are moved apart. In their resting position, the jaws 5, 7 are advantageously kept adjacent each other by means of a spring 8 which acts in compression with its opposite ends inserted in recesses 9, 10 of the handgrips 4, 6.

For the sake of clarity, the jaw 5 will be referred to hereinafter as the lower jaw and the jaw 7 will be referred to as the upper jaw.

A body 12 is articulated at the end of the upper jaw 7 by means of a dowel 11, and has pairs of wings 13, 14 protruding laterally therefrom.

Said body 12 and said wings 13, 14 are guided in a seat 15 provided in the lower jaw 5.

Two rocker levers 18, 19 are articulated between the pairs of wings 13, 14 by means of dowels 16, 17 and comprise respective hook-like elements 20, 21 and extensions 22, 23.

Said hook-like elements 20, 21 are curved and end with opposite claw-like teeth which are pushed towards one another by a small spring 24 interposed between the extensions 22, 23. Said spring 24 is expediently accommodated in a hole 25 which traverses the body 12 and extends between the pairs of wings 13, 14.

As clearly visible in FIGS. 1 and 2, the extensions 22, 23 end with expansions 26, 27 to allow the user of the device to actuate the levers 18, 19.

The described device is completed by two abutments 28, 29 which have a substantially cap-like shape and are advantageously made of a rubber-like material. Said abutments may have various thicknesses and shapes and may be substituted by differently shaped abutments selected according to the variation of the teeth's configuration so as to keep the device in a correct operating position.

The abutments 28, 29 are arranged on opposite sides with respect to the plane of arrangement of the levers 18, 19 and comprise widened parts or pads 30, 31 accommodated or force-fitted in respective seats 32, 33 of the lower face of the jaw 5. Stems 34, 35 extend upwards from the pads and retain the abutments 28, 29 by being inserted into corresponding holes provided in the lower jaw 5.

It should be noted that the portion 36 comprised between the pads 30, 31 is expediently wider than the diameter of the dental crown to be removed. The face of said portion 36 is furthermore slightly depressed with respect to the plane which passes along the surfaces of the pads 30, 31. A recess is thus substantially defined at the portion 36 in the lower jaw 5, and the top of the removed crown can be pushed therein.

The crown to be removed is indicated by the reference numeral 37 in FIGS. 1-4 and is assumed to be located between two molar teeth 38, 39, as more frequently occurs in practice, to exemplify the operation of the device according to the invention.

The user may first examine the area immediately adjacent the crown or prosthesis to be removed and select abutments 28, 29 which are most suitable for engagement therewith. The abutments 28, 29 are then attached to the device by inserting the pads 30, 31, into the seats 32, 33 formed in the lower jaw 5.

The user then places the device so that the crown is opposite to the recess or face 36. Then he spaces the hook-like elements 20, 21 by pressing on the ends 26, 27 against the elastic biasing action or return action exerted by the spring 24. At this stage the device is lowered until the abutments 28, 29, rest on the teeth 38, 39. The hook-like elements 20, 21 engage below the edge of the crown 37 as an effect of the spring 21 upon releasing the levers 22, 23.

By actuating the device, i.e. by moving the handgrips 4, 6 towards each other and consequently moving the jaws 5, 7 apart, the hook-like elements 20. 21 move with respect to the abutments 28, 29 which press by reaction on the teeth 38, 39, while the hook-like elements exert a traction force which extracts the crown. It should be noted that the excursion of the crown is extremely short, since only a slight separation is sufficient to allow its removal. The stroke may in any case be varied by replacing the abutments as required.

As is evident, the invention fully achieves the intended aim and object. In particular, it should be noted that the device allows adjustment of the traction effort according to requirements, without subjecting the patient to traumatic shocks. The extraction of the crown is furthermore also allowed even if one or both of the teeth 38, 39 adjacent to the crown are missing, provided that there are other teeth on which the appropriately selected abutments can rest.

If this is not possible, appropriately shaped abutments are provided so that they can rest on the ginqivae.

We claim:

1. Device for extracting a dental prosthesis, comprising two mutually pivoted levers each having a handgrip and a jaw, a spring arranged between said handgrip and urging said handgrips to move apart, said levers being pivoted so that said jaws are moved apart when the handgrips are actuated mutually closer against the repulsion force of said spring, a seat provided in one of said jaws, a body articulated to the other one of said jaws and guided in said seat, two opposite rocker levers articulated in said body in a plane perpendicular to said jaws, said rocker levers comprising respective extension and opposite hook-like elements adapted to engage an edge of said prosthesis, when said device is placed in extracting position, a hole traversing said body and extending between said extensions, a spring accommodated in said hole and urging said hook-like elements to engage said edge, said jaw provided with said seat having abutments adapted to rest on the teeth adjacent to said prosthesis when said handgrips are moved towards each other, thus causing a resting reaction opposite to the extraction force exerted by said hook-like elements on said prosthesis.

2. Device as claimed in claim 1 wherein said abutments comprise a pair of pads defining a recess therebetween adapted to be engaged by a prosthesis during removal.

3. Device as claimed in claim 1 wherein said body comprises two pairs of wings extending from respective opposite sides of said body and guided in said seat, each pair of wings pivotally supporting a respective rocker lever.

* * * * *